United States Patent [19]

Hentze

[11] 4,214,117
[45] Jul. 22, 1980

[54] FURNACE HEATED BY RADIATION

[75] Inventor: Günter Hentze, Odenthal-Hahnenberg, Fed. Rep. of Germany

[73] Assignee: Bayer Aktiengesellschaft, Leverkusen, Fed. Rep. of Germany

[21] Appl. No.: 869,886

[22] Filed: Jan. 16, 1978

[30] Foreign Application Priority Data

Feb. 5, 1977 [DE] Fed. Rep. of Germany ....... 2704870

[51] Int. Cl.² .............................................. E01D 15/00
[52] U.S. Cl. ..................................... 13/31 R; 13/24; 219/354; 219/408; 219/494; 219/523; 313/340; 432/1
[58] Field of Search ................. 219/216, 121 EB, 220, 219/260, 354, 270, 383, 408, 469, 411, 470, 471, 494, 516, 523, 530, 552, 553; 313/337, 340, 344, 414; 356/85; 13/24, 31; 432/60, 1; 338/241, 296

[56] References Cited

U.S. PATENT DOCUMENTS

| 2,919,373 | 12/1959 | Riley et al. ............................ 313/340 |
| 3,029,360 | 4/1962 | Etter ...................................... 313/340 |
| 3,369,106 | 2/1968 | Troll ....................................... 219/471 |
| 3,401,626 | 9/1968 | Amalfitano ........................ 219/469 X |
| 3,543,002 | 11/1970 | Poole ..................................... 219/354 |
| 3,810,776 | 5/1974 | Banks et al. ..................... 219/469 X |
| 3,890,485 | 6/1975 | Kozbelt ................................ 219/523 |
| 3,895,249 | 7/1975 | Andre et al. ..................... 313/340 X |
| 4,058,697 | 11/1977 | Sokolov ......................... 219/121 EB |

Primary Examiner—Volodymyr Y. Mayewsky
Attorney, Agent, or Firm—Sprung, Felfe, Horn, Lynch & Kramer

[57] ABSTRACT

A furnace which is suitable for analytical measurements is heated by radiation. For this purpose, a radiation source whose radiation is absorbed by the furnace wall is arranged near to the furnace. The furnace is preferably formed as a hollow cylinder which surrounds the radiation source. An incandescent coil may, for example be used as the radiation source.

2 Claims, 3 Drawing Figures

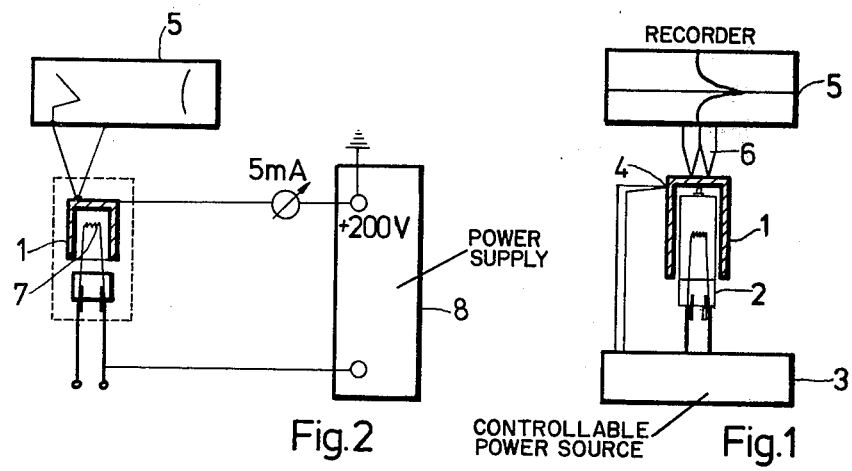
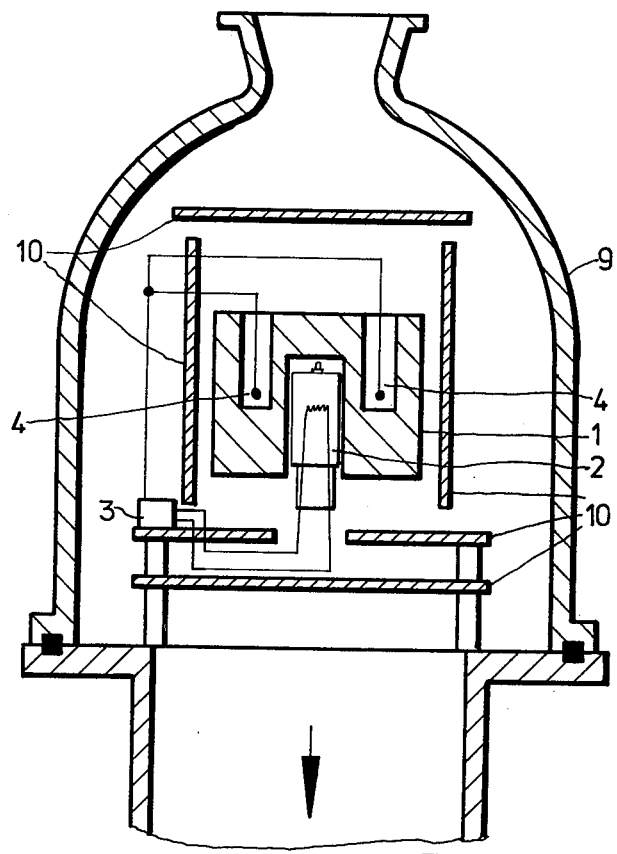

FURNACE HEATED BY RADIATION

The invention relates to a furnace for analytical measurements, in particular differential thermal analysis, mass spectrometry and the production of vapour pressure diagrams. Such furnaces are normally equipped with a filament winding and are heated by the heating effect of the current. The heat transfer from the filament winding to the furnace always causes problems in this process since it only takes place at the relatively few points where the filament winding touches the furnace. Furthermore, an electrical insulation is always required at some point. The insulators used are, moreover, frequently also poor conductors of heat. In the case of jacket heating elements, the insulation is essentially made of $Al_2O_3$-powder which is situated between the heating element and the jacket. In the case of uninsulated heating elements, short circuits of adjacent filament windings and of the filament winding against the furnace are avoided by the use of insulators such as ceramics, mica or asbestos. Most usable insulators evolve a considerable amount of gas in high vacuum ($p \leq 10^{-6}$ mbar) at relatively high temperatures. The vacuum is thus impaired and some measurements can no longer be made or are falsified.

According to the invention there is provided a furnace for analytical measurements, wherein a radiation source whose radiation is absorbed by a furnace wall is arranged adjacent the furnace. The furnace is preferably formed as a hollow cylinder and surrounds the radiation source which is also cylindrical.

The radiation source may be a conventional incandescent lamp or an open incandescent coil when being used in a high vacuum. In an embodiment of the invention the incandescent coil is used as a cathode and furnace wall is used as an anode, heating also being provided by means of the anode dissipation.

The invention is described in more detail below with reference to the accompanying drawing, in which:

FIG. 1 shows a furnace heated by radiation, for differential thermal analysis;

FIG. 2 shows a furnace heated both by radiation and electronically, in a high vacuum; and FIG. 3 shows a furnace heated by radiation installed in a high vacuum differential thermal analysis apparatus.

FIG. 1 shows a furnace 1 which has the shape of a hollow cylinder closed at the top. The cylinder is clamped over an incandescent lamp 2. The furnace is made, for example, of metal, graphite or ceramic material and has a diameter of about 10 mm and a height of about 30 mm. The lamp 2 is a quartz lamp which is heated by a control instrument 3 at a power of 50 to 150W. The heating power is regulated by a thermoelement 4 placed on the exterior of the furnace. The radiation emanating from the incandescent lamp is almost completely absorbed in the overall range of wavelength and solid angle. The difference thermal analysis measurement is made on the upper face of the furnace by means of a thermoelement 6 connected to a potentiometer-type recorder 5.

FIG. 2 shows a hollow cylindrical furnace 1 at a high vacuum. An incandescent coil 7 which is arranged inside the hollow cylinder is advantageously used as a radiation source. If the incandescent coil 7 is connected as a cathode and the furnace as an anode, then the furnace may also be heated by an electron flow of 5 mA at a voltage of 200 V supplied by a power supply 8.

In FIG. 3, a furnace heated by radiation is inserted in a high vacuum apparatus. The incandescent lamp 2 and the furnace 1, including the thermoelement 4, are installed in a high vacuum container 9. In order to shield the exterior from the radiation of the furnace, radiation screens 10 are arranged around the furnace 1.

The main advantage of a furnace of this type lies in its low thermal capacity. The furnace may only weigh, for example, from 5 to 50 g, depending upon the material used. A thermal capacity of the order of magnitude of from 0.5 to 10 cal° $C.^{-1}$ are produced when the specific heat of the oven material is from from 0.1 to 0.5 cal $g^{-1}$. Owing to this low thermal capacity, such a furnace may be regulated very rapidly. The power required for heating is low and is generally well below 50 W, depending upon the heating rate. Very high temperatures may be obtained with relatively low power by using effective radiation reflectors or radiation screens around the furnace (owing to the melting point of quartz and platinum, maximum 1600° C.).

What we claim is:

1. A furnace for analytical measurements comprising:
   (a) a radiation source comprising an incandescent lamp,
   (b) a hollow cylinder composed of one from the group of metal, graphite and ceramic material spaced apart from and surrounding the incandescent lamp for absorbing the radiation emitted therefrom,
   (c) temperature sensing means attached to the outside of the hollow cylinder for monitoring the temperature at its surface,
   (d) a regulatable power supply connected to the incandescent lamp and to the temperature sensing means and regulated in response to the monitored temperature,
   (e) a container enclosing the lamp, cylinder and temperature sensing means with an inert atmosphere therein, and
   (f) the overall heat capacity of the furnace is in the range of 0.5–10 cal/° C.

2. The furnace according to claim 1, wherein the container is a high vacuum container with a high vacuum atmosphere therein.

* * * * *